United States Patent [19]

Claude et al.

[11] Patent Number: 5,652,197
[45] Date of Patent: Jul. 29, 1997

[54] GLYPHOSATE COMPOSITIONS

[75] Inventors: Jean-Pierre Claude, Overijse; Shuaib Ahmad Khan; Robert William Mitchell, both of Brussels, all of Belgium

[73] Assignee: Monsanto Company, St. Louis, Mo.

[21] Appl. No.: 696,024

[22] Filed: Aug. 9, 1996

Related U.S. Application Data

[60] Continuation of Ser. No. 456,258, May 31, 1995, abandoned, which is a division of Ser. No. 311,824, Sep. 23, 1994, Pat. No. 5,464,807, which is a division of Ser. No. 649,105, Feb. 1, 1991, abandoned.

[30] Foreign Application Priority Data

Feb. 5, 1990 [GB] United Kingdom .................. 9002495

[51] Int. Cl.$^6$ ........................... A01N 25/30; A01N 57/04
[52] U.S. Cl. ......................... 504/206; 71/DIG. 1
[58] Field of Search ............................. 504/206

[56] References Cited

U.S. PATENT DOCUMENTS

| | | | |
|---|---|---|---|
| 3,123,641 | 3/1964 | Longley | 260/567.6 |
| 3,141,905 | 7/1964 | Longley | 260/567.6 |
| 4,159,901 | 7/1979 | Beestman et al. | 71/86 |

OTHER PUBLICATIONS

Wyrill et al. "Glyphosate Toxicit, . . . as Influenced by Surfactants." *Weed Science* 25(3):275–287. May 1977.

*Primary Examiner*—S. Mark Clardy
*Attorney, Agent, or Firm*—Stanley M. Tarter; Arnold, White & Durkee

[57] ABSTRACT

The composition of the invention comprises a glyphosate herbicide and a quaternary ammonium compound the latter having the formula

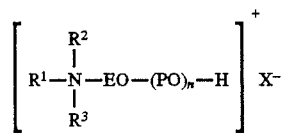

wherein —EO— means an ethylene oxide radical and —PO— means a propylene oxide radical, $R^1$ and $R^2$ are each independently an alkyl group having from 1 to 3 carbon atoms; $R^3$ is an alkyl group having from 1 to 3 carbon atoms, a group having the formula $(EO)_m$—H or a group having the formula EO—$(PO)_m$—H; n (in a compound in which $R^3$ is an alkyl group) or n+m (in a compound in which $R^3$ is a group having the formula EO—$(PO)_m$—H), has a value of from about 2 to about 20; and $X^-$ is a suitable anion.

7 Claims, No Drawings

GLYPHOSATE COMPOSITIONS

This application is a continuation application of U.S. patent application Ser. No. 08/456,258 filed May 31, 1995, now abandoned, which is a divisional application of U.S. patent application Ser. No. 08/311,824 filed Sep. 23, 1994, now U.S. Pat. No. 5,464,807, which is a divisional application of abandoned U.S. patent application Ser. No. 07/649,105 filed Feb. 1, 1991.

This invention relates to an agriculturally acceptable glyphosate composition, more particularly to such compositions containing a glyphosate herbicide and a surfactant which enhances the herbicidal activity of the glyphosate herbicide. This invention also relates to the use of such compositions to kill or control unwanted and undesired vegetation. More particularly, such compositions contain a herbicidally effective amount of glyphosate.

Numerous studies have been made on the effect of additives on the herbicidal action of glyphosate. For example Wyrill and Burnside, Weed Science, Vol. 25 (1977), 275–287, examined solutions containing different classes of surfactant, including polyoxyethylene stearyl methyl ammonium chlorides containing respectively 2 and 15 oxyethylene units. Some classes of surfactant were more effective than others in enhancing the herbicidal effect of glyphosate (used as a solution of the isopropylamine salt), but Wyrill and Burnside concluded that an effective surfactant is a critical component of any glyphosate spray mixture.

Commercially sold glyphosate formulations generally contain a surfactant. These formulations are safe herbicidal formulations from the point of view of lack of toxicity and environmental acceptability. Moreover, the level of toxicity or irritancy which is shown in certain situations, for example commercial glyphosate formulations containing an ethoxylated tallow amine surfactant, which have some toxicity to aquatic life, is essentially due to the presence of the ethoxylated tallow amine surfactant and not due merely to the glyphosate itself.

This invention satisfies the need for an improved glyphosate formulation. In this invention currently employed surfactants are advantageously replaced by other surfactants which provide a similar efficacy enhancing effect to the herbicidal activity of glyphosate but also provide lower irritancy and toxicity than currently employed surfactants.

Ammonium salts such as ammonium sulphate (Turner and Loader, Weed Research, Vol. 20 (1980), 139–146) and ammonium thiocyanate (U.S. Pat. No. 4,612,034) have also been shown to further enhance the herbicidal activity of glyphosate salt formulations containing surfactants.

EP-A-0 290 416 allegedly discloses improved glyphosate formulations containing alkoxylated amine surfactants, more particularly alkoxylated tallow amine surfactants, and possibly ammonium sulfate. The additives disclosed are said to enhance visibly the glyphosate activity. The formulations disclosed are said to show low toxicity characteristics against the organisms, partially due to lower content of surfactant.

We have discovered that certain polyoxyalkylene quaternary ammonium compounds (disclosed hereinafter) are very effective in enhancing the herbicidal activity of glyphosate, and that improved glyphosate formulations containing such quaternary ammonium compounds are relatively non-toxic and non-irritant. We have also found that our new glyphosate formulations provide reduced foaming in comparison with known glyphosate formulations.

U.S. Pat. Nos. 3,141,905, 3,123,641 and 3,123,640 disclose some particular polyoxyalkylated quaternary ammonium surfactants. The use of these types of surfactants in glyphosate compositions is however not disclosed nor suggested. Further, no toxicity or irritancy data in herbicide compositions are disclosed. British patents No. 1 421 133, 1 462 043, 1 470 618, 1 450 531, 1 453 443, EP-A-0 066 946, WO-87/04595, GB-A-2 113 093, GB-A-2 059 773 and GB-A-2 047 098 disclose quaternary ammonium surfactants in pesticide formulations, but none of them discloses or suggests applicant's composition of glyphosate herbicide with a quaternary ammonium surfactant(s) disclosed herein.

European patent No. 0 206 537 discloses the use of Emcol-CC 57, a polypropoxylated quaternary ammonium surfactant, in solid phytoactive glyphosate compositions.

A composition of the invention comprises a glyphosate herbicide and a quaternary ammonium compound having the formula:

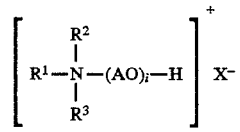

wherein A or each A represents an alkylene group having 2 or 3 carbon atoms, $R^1$ and $R^2$ are each independently an alkyl group having from 1 to 5 carbon atoms; $R^3$ is an alkyl group having from 1 to 5 carbon atoms or a group having the formula $(AO)_i$—H; i (in a compound in which $R^3$ is an alkyl group) or i+j (in a compound in which $R^3$ is a group having the formula $(AO)_j$—H) has a value of from 2 to 20; and $X^-$ is a suitable anion.

A preferred composition of the invention comprises a glyphosate herbicide and a quaternary ammonium compound the latter having a structure represented by the formula:

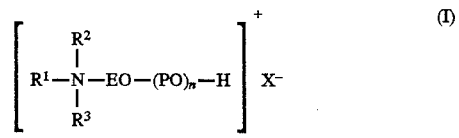

wherein —EO— is an ethylene oxide radical and —PO— is a propylene oxide radical, $R^1$ and $R^2$ are each independently an alkyl group having from 1 to 3 carbon atoms; $R^3$ is an alkyl group having from 1 to 3 carbon atoms, a group having the formula $(EO)_m$—H or a group having the formula EO—$(PO)_m$—H; n (in a compound in which $R^3$ is an alkyl group) or n+m (in a compound in which $R^3$ is a group having the formula EO—$(PO)_m$—H), has a value of from 2 to 20; and $X^-$ is a suitable anion and n and m are each independently varying integers.

By a "suitable" anion is meant an anion such that applicant's composition is classified both as "non-irritant" when evaluated by a standard test procedure involving dermal and ocular tissue of the rabbit, and as "relatively non-toxic" to fish when evaluated by standard test procedures both hereinafter identified.

The compositions of this invention containing quaternary ammonium compounds as disclosed herein are non irritant and have relatively low toxicity. For example, they are less irritant and less toxic than compositions containing a glyphosate herbicide and a comparable amount of an ethoxylated fatty amine surfactant, one of the classes of surfactant (s) previously considered optimum for glyphosate enhancement.

Compared to alkyl polyglycoside surfactants known for their low eye irritancy characteristics in cosmetics for instance, and previously disclosed in liquid glyphosate compositions (see EP-A-0 220 902 and EP-A-0 364 202) the formulations according to our present invention provide comparatively much reduced foaming. Our invention reduces or eliminates the need for an antifoam ingredient such as a silicone antifoam agent. Without antifoam in the formulation, the need to shake the formulation of this invention before use is reduced or eliminated. This is of especial advantage when the formulation is to be sold in large containers.

Furthermore the compositions of our invention provide stable tank mixing with other pesticides and particularly herbicides. More especially the compositions according to the invention show good compatibility with triazines.

The number of propylene oxide units of the quaternary amine symbolized in Formula (I) is preferably in the range from 2 to about 20 as the advantages of this invention are more pronounced in that range.

Herein, the term "glyphosate herbicide" means N-phonomethyl-glycine (glyphosate) and any form or derivative of glyphosate which in aqueous solution provides glyphosate anions. Suitable cations may also be present.

Examples of such suitable cations are alkali metal cations, for instance sodium and potassium, and ammonium and substituted ammonium cations. The latter include cations derived from primary or secondary amines such as isopropylamine or dimethylamine, and from diamines such as ethylenediamine.

Especially preferred as a glyphosate herbicide are water soluble salts of glyphosate such as the isopropylamine salt of glyphosate and the trimethylsulfonium salt of glyphosate. U.S. Pat. No. 3,799,758 dicloses salts of glyphosate useful herein. Other examples of agriculturally acceptable salts of glyphosate are aminoguanidine salts as disclosed in EP-A-0 088 180. Because glyphosate has more than one replaceable hydrogen atom, mono- and di-alkali metal salts are possible, as well as mixtures of such salts.

Especially preferred quaternary ammonium compounds for use in the present invention are those having a structure of Formula (I) wherein n has a value from 4 to 15 or n+m has a value from 3 to 14 and —PO— is isopropylene oxide.

Quaternary ammonium compounds available in practice are not necessarily pure compounds in the sense of consisting of a single molecular species. In any particular instance, several different compounds where n or n and m vary over a narrow range will normally be present, so that the values of n and n+m mentioned above are understood as average values.

The anion symbolized as $X^-$ in Formula (I) symbolizing a quaternary ammonium compound used in a composition of the invention can be for example a halide ion, for instance chloride or bromide, phosphate, or methylsulphate, or ethylsulphate, or a a glyphosate ion. Other suitable anions include acetate, lactate, dimethyl phosphate or polyalkoxylated phosphate and the like.

Particularly good results have been obtained with quaternary ammonium compounds having the above general Formula (I) wherein $R^1$ and $R^2$ are each methyl, $X^-$ is $Cl^-$, and where (i) $R^3$ is EO—$(PO)_m$—H and n+m has an average value of about 6; (ii) $R^3$ is methyl, and n has an average value of 6.3; or (iii) $R^3$ is methyl and n has a value of about 8.

In the compositions of this invention, the weight ratio of glyphosate (expressed as glyphosate acid equivalent) to the quaternary ammonium compound can vary over a considerable range, for example from about 1:5 to about 10:1. The optimum ratio will vary according to the manner in which the herbicidal composition is applied, the weed species to be treated, and the particular quaternary ammonium compound selected, but is normally within the range from about 1:2 to about 4:1, for example about 1:1 or about 2:1.

A composition of the invention can be a liquid aqueous concentrate intended to be diluted with water to form a spray solution for the actual herbicidal application. A liquid concentrate will normally contain at least 50 grams glyphosate acid equivalent per liter, and preferably at least 100 g/l. Compositions of the invention may include a significant amount of an agriculturally-acceptable inorganic ammonium salt such as ammonium sulphate, in addition to the glyphosate and quaternary ammonium compound. Liquid concentrates without such an inorganic ammonium salt can contain up to 450 g/l or more, for example 300–450 g/l, glyphosate acid equivalent when the glyphosate is present as a salt having a high solubility, for example the isopropylamine salt. In liquid concentrates containing an inorganic ammonium salt (for example ammonium sulphate in an amount of from 100 to 500 g/l), the maximum amount of glyphosate which can be accommodated is less, and may be, for example, about 150 g/l glyphosate acid equivalent.

In another form, a composition of the invention is a solid, for example a free-flowing particulate, granular solid or compressed into tablets or briquets of any desired size and shape. The term "solid" as employed herein includes granular, particular, wettable powder, water soluble and water dispersible, mixtures thereof and the like. Typically such solids are dry. Such dry compositions will usually contain not more than 5% and preferably not more than 1% by weight of water.

In a solid composition, glyphosate is preferably present as the isopropylamine salt or an alkali metal salt such as a sodium or potassium salt, or as an ammonium salt. The surfactant used in the compositions of the invention is particularly suitable for dry formulations.

Optionally solid compositions may be formulated to include a water-soluble inert carrier, and for this purpose ammonium sulphate is particularly suitable. The weight ratio of glyphosate (expressed as glyphosate acid equivalent) to quaternary ammonium compound in such compositions will be within the general range mentioned above. The amount of water-soluble inert carrier is not critical, and in the case of ammonium sulphate, the amount may, for example, range from 20% to 80% of the total weight of the composition. Solid compositions can be made, for example by spray drying an aqueous solution of the components, by dry-blending the ingredients in conventional blending apparatus, or by extrusion blending whereby a granular product is obtained in an essentially single operation. In a preferred method, an alkali metal salt of glyphosate is prepared in situ by the method of European patent application 8790 1321.7. It has been found that by radial extrusion, a product is obtained with better dissolution characteristics in water compared to a product with frontal extrusion.

Compositions of the invention also include solutions which may be applied by spraying for example. In these solutions, the concentration of glyphosate is selected according to the volume per unit area of spray solution to be used and the desired rate of application of glyphosate per unit area. For example, conventional spraying is done at 100–600 liters of spray solution per hectare, and the rate of application of glyphosate is typically 0.125 to 1.5 kg of glyphosate acid equivalent per hectare. In controlled drop spraying, the rate of application of glyphosate per hectare will normally be in the same range, but the volume of spray solution per hectare will be considerably less, perhaps 15–50 liters per hectare. Spray solutions for controlled drop spraying are therefore more concentrated than those used in conventional spraying. In spray solutions containing inorganic ammonium salts in addition to the glyphosate and quaternary ammonium compound, the amount of inorganic ammonium salt which can be included may be, for example, up to 10 times the weight of glyphosate acid equivalent.

Spray solution compositions can be prepared by diluting liquid concentrates or dissolving solid compositions as described above, or by tank mixing the separate components of the compositions.

Compositions of the invention can optionally contain other components, preferably those which do not have an adverse effect on the resulting composition as to irritancy and toxicity. These additional components may include anti-freeze agents such as ethylene glycol, polyethylene glycols and glycerol. Other examples of additional components are dyes, thickening agents, anti-foam agents, for instance silicone-based anti-foam agents, agents suitable for pH adjustment to optimize herbicidal efficacy and stability of the composition, and certain surfactants, for instance non-ionic surfactants such as polyoxy-ethylene ethers or esters, and sugar ethers. Concentrates and solutions of the invention may also be mixed with one or more herbicides, themselves preferably having low or no irritancy and relatively low toxicity.

Some of the quaternary ammonium compounds shown in Table 1 following were used to prepare compositions in turn used in investigating their potentiating effect on the herbicidal action of glyphosate.

TABLE 1

| | Quaternary Amine | | | Average |
|---|---|---|---|---|
| No. | $R^1$ | $R^2$ | $R^3$ | $X^-$ | $n + m$ |
| 1 | $C_2H_5$ | $C_2H_5$ | $CH_3$ | $Cl^-$ | 8 |
| 2 | $CH_3$ | $CH_3$ | —EO—$(PO)_m$—H | $Cl^-$ | 6 |
| 3 | $CH_3$ | $CH_3$ | —EO—$(PO)_m$—H | $Cl^-$ | 8 |
| 4 | $CH_3$ | $CH_3$ | —EO—$(PO)_m$—H | $Cl^-$ | 9.7 |
| 5 | $CH_3$ | $CH_3$ | $CH_3$ | $Cl^-$ | 6.3 |
| 6 | $CH_3$ | $CH_3$ | $CH_3$ | $Cl^-$ | 8 |
| 7 | $CH_3$ | $CH_3$ | $CH_3$ | $CH_3SO_4^-$ | 8.4 |
| 8 | $CH_3$ | $CH_3$ | $CH_3$ | $Cl^-$ | 3 |
| 9 | $CH_3$ | $CH_3$ | $CH_3$ | $Cl^-$ | 14.2 |
| 10 | $C_3H_7$ | $C_3H_7$ | $CH_3$ | $CH_3SO_4^-$ | 8 |
| 11 | $CH_3$ | $CH_3$ | $CH_3$ | $CH_3COO^-$ | 8 |
| 12 | $CH_3$ | $CH_3$ | $CH_3$ | $PO_4(CH_3)_2^-$ | 8 |
| 13 | $CH_3$ | $CH_3$ | $CH_3$ | Lactate | 8 |
| 14 | $CH_3$ | $CH_3$ | $CH_3$ | $Cl^-$ | 20 |
| 15 | $CH_3$ | $CH_3$ | $CH_3$ | $Cl^-$ | 8 |
| 16 | $CH_3$ | $C_2H_5$ | $C_2H_5$ | $Cl^-$ | 7 |

Table 2 below shows the components and their concentrations in examples of prepared compositions of the invention which are liquid concentrates. The glyphosate is employed in the compositions as the isopropylamine salt of glyphosate, and the concentration of the isopropylamine salt glyphosate is expressed as glyphosate acid equivalent (a.e.).

TABLE 2

| COMPOSITION | QUATERNARY AMINE | | GLYPHOSATE A.E. |
|---|---|---|---|
| No. | No. | Conc. (g/l) | Conc. (g/l) |
| 1 | 2 | 180 | 360 |
| 2 | 2 | 200 | 400 |
| 3 | 2 | 225 | 450 |
| 4 | 5 | 180 | 360 |

TABLE 2-continued

| COMPOSITION | QUATERNARY AMINE | | GLYPHOSATE A.E. |
|---|---|---|---|
| No. | No. | Conc. (g/l) | Conc. (g/l) |
| 5 | 5 | 200 | 400 |
| 6 | 5 | 225 | 450 |
| 7 | 6 | 180 | 360 |
| 8 | 6 | 200 | 400 |
| 9 | 6 | 225 | 450 | g/l = grams per liter.

Examples of two solid compositions of this invention are shown in Table 3 below.

TABLE 3

| | Composition No. | |
|---|---|---|
| | 10 | 11 |
| Components | (% by weight) | |
| Glyphosate sodium salt | 24.03 | 39.48 |
| Quaternary amine No. 6 (TABLE I) | 10.63 | 17.50 |
| Ammonium sulphate | 63.79 | 40.80 |
| Silicone defoamer | 0.08 | 0.12 |
| Water | 0.50 | 0.50 |
| Inert(s) | 0.97 | 1.60 |

The herbicidal effectiveness of spray solutions prepared by the dilution of some of the liquid concentrates exemplified above was evaluated as follows:

For greenhouse tests, plants were grown from seed in 13 cm pots containing a natural sandy loam soil enriched with a mixture of fertilizer. All irrigation was supplied automatically from below. The environment was controlled at a temperature regime of 18° C. (day), 12° C. (night), a relative humidity of 65% day and 75% night, and an illuminance of 1500 microeinsteins $m^{-2}s^{-1}$ (with an artificial shading if natural light gave more, and an artificial supply if the natural light was less than 1300 microeinstein $m^{-2}s^{-1}$).

Before spraying, pots were selected for uniformity as far as possible, and atypical examples were discarded. Spray solutions were applied with a Mardrive precision laboratory sprayer, calibrated to deliver spray solution in one pass at a rate equivalent to 200 l/ha. All replicate pots (3–5 replicates per species, per treatment) were sprayed with one pass of the sprayer.

After treatment, control pots were placed at random among treated pots. Assessments of "% phytotoxicity" were made by comparison with untreated controls and with Controls* sprayed with a glyphosate solution containing an ethoxylated tallow amine surfactant in a weight ratio of 2:1 glyphosate a.e.:surfactant, on an arbitrary scale from 0 to 100%, where 0 means no visible effect and 100% means death of all plants. For any one assessment, all pots were rated by the same individual, assessments being performed "blind", without knowledge of the treatment.

Results were as follows. The results in Table 4 for % phytotoxicity represent the average of 3 rates (200, 400 and 600 g glyphosate a.e./ha)×3 replicates, 34 days after treatment for each quaternary amine (designation from Table 1).

TABLE 4

| Quaternary No. | Lolium multiflorum | Geranium molle |
| --- | --- | --- |
| 1 | 32 | 36 |
| 2 | 45 | 47 |
| 3 | 29 | 35 |
| 4 | 32 | 36 |
| 5 | 46 | 51 |
| 6 | 44 | 45 |
| Control* | 34 | 41 |

The results in Table 5 for the % phytotoxicity are the average of 3 rates (200, 400 and 600 g glyphosate e.e./ha)×3 replicates, 30 days after treatment.

TABLE 5

| Quaternary No. | Elymus repens |
| --- | --- |
| 2 | 43 |
| 3 | 39 |
| 4 | 52 |
| 6 | 55 |
| Control* | 46 |

A field test was carried out in a sown 90 m² pasture containing a mixture of perennial ryegrass and blackgrass for the narrow leaved species (grasses) and a mixture of Sinapis arvensis Matricaria sp. and Trifolium repens broadleaves. This was sprayed at a spray volume application rate equivalent to about 400 l/ha, and at an air temperature of about 18° C. No rain was noted for 5 days after spraying. The test design was a complete randomized block design with 3 replicates of each treatment and one untreated plot per 4 treated plots. The results in Table 6 below for the % phytotoxicity are the average of 3 rates (800, 1200 and 1600 g glyphodate a.e./ha)×3 replicates, 30 days after treatment.

TABLE 6

| Quaternary No. | Grasses | Broadleaves |
| --- | --- | --- |
| 2 | 45 | 49 |
| 6 | 40 | 45 |
| Control* | 42 | 47 |

Compositions containing the quaternary Nos. 2, 5 and 6 of this invention in these tests (Table 4, 5 and 5) show comparable efficacy to the Control* composition therein. Thus in considering these data, these phytotoxicity tests show that Quaternaries Nos. 2, 5 and 6 enhanced the performance of glyphosate to a similar degree as did the ethoxylated fatty amine surfactant of the Control.

Standard skin and eye irritancy tests were carried out using compositions Nos. 2, 5 and 8 on New Zealand white rabbits by the procedures of OECD Guidelines for Testing of Chemicals, Tests No. 404 "Acute Dermal Irritancy/ Corrosion", 12 May 1981, and 405 "Acute Eye Irritancy/ Corrosion" 24 Feb. 1987, respectively. When the results were assessed according to the criteria of European Commission Directive 83/467/EEC, all the compositions were classified as non-irritant to both dermal and ocular tissue.

The same compositions were examined for toxicity to fish by the procedure of OECD Guidelines for Testing of Chemicals, Test No. 203, 4 Apr. 1984, "Fish Acute Toxicity Test". When the results were assessed on the Proposed Toxicity Rating Scale for Use at CNFRL (Columbia National Fisheries Research Laboratory, U.S.A.) the compositions were classified as "relatively non-toxic".

Quaternary amines designated in Table 1 as numbers 6–10 were tested in another field test in Summer. The rates of glyphosate (as glyphosate isopropylamine salt) application were equivalent to about 300, 600 and 900 g a.e./ha. The application was made at about 250 l/ha using standard field spraying equipment. The ratio of glyphosate acid equivalent surfactant was about 2/1. The weed assessed is Trifolium repens (TRFRE).

The weather at the spraying was clear and hot, no wind. Temperature was around 30° C. and no rain was recorded in six hours following spraying.

Assessment of percent phytotoxicity was made by comparison with untreated control plots on an arbitrary scale from 0 to 100%, where 0 means no visible effect and 100 means death of all plants.

Randomised block design with 3 replicates was used (1 check per 5–6 treatment plots). Unit plot size=1.5 m×3.5 m.

TABLE 7

| Quaternary Amine No | Glyphosate g. a.e./ha | TRFRE 32 DAT$^{xxx}$ |
| --- | --- | --- |
| Control* | 300 | 35 |
|  | 600 | 47 |
|  | 900 | 53 |
| 6 | 300 | 25 |
|  | 600 | 38 |
|  | 900 | 55 |
| 7 | 300 | 27 |
|  | 600 | 38 |
|  | 900 | 50 |
| 10 | 300 | 23 |
|  | 600 | 35 |
|  | 900 | 47 |
| 9 | 300 | 25 |
|  | 600 | 48 |
|  | 900 | 50 |
| 8 | 300 | 18 |
|  | 600 | 33 |
|  | 900 | 45 |

DAT$^{xxx}$ = days after treatment.

The quaternary amines numbered 6–10 in TABLE 2 in a series of 2/1 glyphosate acid equivalent/surfactant compositions were also tested in a further greenhouse test. The conditions were the same as previously. The rates of application were 360, 540 and 1080 g a.e./ha (glyphosate in the form of the isopropylamine salt).

Results are shown in table 8.

TABLE 8

| Quaternary No. | Rate g a.e./ ha | BRSNW (DAT) | | | GERMO (DAT) | | | LOLRI (DAT) | | AGGRE (DAT) | |
| --- | --- | --- | --- | --- | --- | --- | --- | --- | --- | --- | --- |
|  |  | 14 | 20 | 36 | 14 | 20 | 36 | 20 | 36 | 20 | 36 |
| 7 | 360 | 17 | 27 | 39 | 15 | 60 | 85 | 47 | 77 | 70 | 90 |
|  | 540 | 23 | 38 | 58 | 35 | 70 | 93 | 92 | 100 | 75 | 82 |

TABLE 8-continued

| Quaternary No. | Rate g a.e./ ha | BRSNW (DAT) | | | GERMO (DAT) | | | LOLRI (DAT) | | AGGRE (DAT) | |
|---|---|---|---|---|---|---|---|---|---|---|---|
| | | 14 | 20 | 36 | 14 | 20 | 36 | 20 | 36 | 20 | 36 |
| | 1080 | 47 | 63 | 78 | 40 | 75 | 98 | 83 | 100 | 77 | 100 |
| 10 | 360 | 30 | 42 | 42 | 27 | 65 | 80 | 55 | 85 | 60 | 82 |
| | 540 | 47 | 55 | 65 | 43 | 73 | 88 | 67 | 92 | 75 | 87 |
| | 1080 | 45 | 62 | 75 | 55 | 78 | 95 | 99 | 100 | 78 | 100 |
| 9 | 360 | 30 | 23 | 35 | 15 | 33 | 60 | 58 | 82 | 63 | 75 |
| | 540 | 37 | 55 | 58 | 50 | 60 | 75 | 60 | 93 | 73 | 93 |
| | 1080 | 53 | 78 | 95 | 53 | 65 | 78 | 88 | 100 | 83 | 100 |
| 8 | 360 | 10 | 20 | 8 | 10 | 35 | 75 | 50 | 85 | 47 | 73 |
| | 540 | 25 | 20 | 12 | 33 | 63 | 95 | 63 | 97 | 70 | 87 |
| | 1080 | 28 | 45 | 60 | 48 | 73 | 100 | 80 | 98 | 82 | 97 |
| 6 | 360 | 12 | 20 | 33 | 15 | 70 | 80 | 52 | 87 | 77 | 93 |
| | 540 | 30 | 40 | 52 | 40 | 65 | 85 | 83 | 95 | 85 | 100 |
| | 1080 | 37 | 68 | 83 | 50 | 70 | 90 | 83 | 98 | 82 | 98 |
| Control* | 360 | 17 | 20 | 37 | 8 | 35 | 65 | 62 | 92 | 65 | 80 |
| | 540 | 42 | 57 | 65 | 40 | 68 | 100 | 87 | 100 | 85 | 100 |
| | 1080 | 50 | 67 | 75 | 58 | 80 | 100 | 93 | 100 | 73 | 100 |

The assessed weeds are:
BRSNW Brassica (oil seed rape)
GERMO Geranium molle
LOLRI Lolium rigidum
AGGRE Agropyron repens (couch)

The results are shown in the previous Tables 7 and 8 indicate that the glyphosate phytotoxicity of compositions of the invention employed herein is enhanced to a level comparable to that of the Control* composition.

Compositions of the invention are particularly compatible with other herbicides and show good stability characteristics when mixed with one or more other herbicides. Also tank mix properties appeared very good.

In a compatibility test, the following formulations were used:

| Composition | Ingredient | Amount of Composition Employed with Ingredient |
|---|---|---|
| (1) | Glyphosate + Quaternary amine (2) | 6 L$^{xx}$ in 400 L |
| (7) | Glyphosate + Quaternary amine (6) | 6 L in 400 L |
| GESATOPE | Simazine | 6 L in 400 L |
| CENT - 7 | Isoxaben | 8 L in 400 L |
| SEXTAN | Isoxaben/Simazine | 7.5 L in 400 L |
| VITIDOR | Oryzalin/Simazine | 12 L in 400 L |
| FENICAN | Diuron/Terbuthylazine | 6 L in 400 L |
| ZORIAL | Morflurazon | 2.5 kg in 400 L |
| GOLTIX | 70% Metamitron | 5 kg in 400 L |
| PYRAMIN | 65% Chloridazon | 5 kg$^{xxx}$ in 400 L |

The coherbicide was mixed with water and then composition (1) or (7) was added and the mixture thoroughly mixed. Observations were made at 1, 5, 10, 30 and 60 minutes after mixing. Final evaluation was done after two hours. No compatibility agent was added.
L$^{xx}$=liter
kg$^{xxx}$=Kilogram

COMPATIBILITY TEST

| MIXTURE No. | after 1 min.$^x$ | after 5 min. | after 10 min. | after 30 min. | after 60 min. | after 2 hours |
|---|---|---|---|---|---|---|
| (1) + Gesatope | OK | OK | OK | sed/red | Sed/red | Sed/red |
| (1) + Cent - 7 | OK | OK | OK | OK | Sed/red | Sed/red |

-continued

COMPATIBILITY TEST

| MIXTURE No. | after 1 min.$^x$ | after 5 min. | after 10 min. | after 30 min. | after 60 min. | after 2 hours |
|---|---|---|---|---|---|---|
| (1) + Sextan | OK | OK | OK | OK | Sed/red | Sed/red |
| (1) + Vitidor | OK | OK | OK | OK | Sed/red | Sed/red |
| (1) + Fenican | OK | OK | OK | OK | Sed/red | Sed/red |
| (1) + Zorial | OK | OK | OK | OK | Sed/red | Sed/red |
| (1) + Goltix | OK | OK | OK | OK | Sed/red | Sed/red |
| (1) + Pyramin | OK | OK | OK | OK | Sed/red | Sed/red |
| (7) + Gesatope | OK | OK | OK | Sed/red | Sed/red | Sed/red |
| (7) + Cent-7 | OK | OK | OK | OK | Sed/red | Sed/red |
| (7) + Sextan | OK | OK | OK | OK | Sed/red | Sed/red |
| (7) + Vitidor | OK | OK | OK | OK | Sed/red | Sed/red |
| (7) + Fenican | OK | OK | OK | OK | Sed/red | Sed/red |
| (7) + Zorial | OK | | | Tr.sed | Sed/red | Sed/red |
| (7) + Goltix | OK | OK | OK | Sed/red | Sed/red | Sed/red |
| (7) + Pyramin | OK | OK | OK | OK | Sed/red | Sed/red |

OK = No Compatibility Problems
Tr.sed = Trace of Sedimentation
Sed/red = Sedimentation but Easily Re-dispersible
min. = Minutes As an advantage, compositions of this invention may contain suitable coherbicides including sulfonyl ureas depending on the intended use of the composition containing the coherbicide(s).

What is claimed is:

1. A foliar applied composition which comprises a glyphosate herbicide in a herbicidally effective amount and a quaternary ammonium compound having the formula:

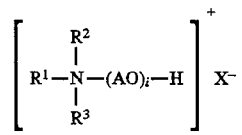

wherein A or each A represents an alkylene group having 2 or 3 carbon atoms, $R^1$ and $R^2$ are each independently an alkyl group having from 1 to 5 carbon atoms; $R^3$ is an alkyl group having from 1 to 5 carbon atoms or a group having the formula $(AO)_j$—H; i (in a compound in which $R^3$ is an alkyl group) or i+j (in a compound in which $R^3$ is a group having the formula $(AO)_j$—H) has a value of from 2 to 20; and $X^-$ is a suitable anion; said ammonium compound being present in an amount sufficient to enhance the herbicidal effectiveness of the glyphosate herbicide; whereby water based formulations of the composition have reduced foam when sprayed.

2. A foliar applied composition comprising a glyphosate herbicide and a quaternary ammonium compound the latter compound having the formula:

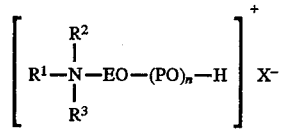

wherein —EO— means an ethylene oxide radical and —PO— means a propylene oxide radical, $R^1$ and $R^2$ are each independently an alkyl group having from 1 to 3 carbon atoms; $R^3$ is an alkyl group having from 1 to 3 carbon atoms, a group having the formula $(EO)_m$—H or a group having the formula EO—$(PO)_m$—H; n (in a compound in which $R^3$ is an alkyl group) or n+m (in a compound in which $R^3$ is a group having the formula EO—$(PO)_m$—H), has a value of from about 2 to about 20; and $X^-$ is a suitable anion; said ammonium compound being present in an amount sufficient to enhance the herbicidal effectiveness of the glyphosate herbicide; whereby water based formulations of the composition have reduced foam when sprayed.

3. A composition according to claim 2 wherein, in the formula of the quaternary ammonium compound, —PO— means isopropylene oxide and n (in a compound in which $R^3$ is a methyl or ethyl group) has a value of from 4 to 15, and n+m (in a compound in which $R^3$ is a group having the formula EO—$(PO)_m$) has a value of from 3 to 14 and $X^-$ is halide, ethylsulfate, methylsulfate, dimethylphosphate, polyalkoxyphosphate, lactate or acetate.

4. A composition according to claim 1 in which the weight ratio of glyphosate (expressed as glyphosate acid equivalent) to the quaternary ammonium compound is in the range from about 1:2 to about 4:1.

5. The composition according to claim 4 in which the glyphosate is present as the isopropylamine salt or the trimethylsulfonium salt of glyphosate.

6. A composition according to claim 5 which is a liquid concentrate containing at least 100 g/l of glyphosate expressed as glyphosate acid equivalent.

7. A composition according to any of claims 1, 2, 3, 4, 5 or 6 which is a spray solution having a concentration such that when sprayed at 100–600 liters per hectare, 0.125 to 1.5 kg of glyphosate (expressed as glyphosate acid equivalent) per hectare is applied.

* * * * *

UNITED STATES PATENT AND TRADEMARK OFFICE
CERTIFICATE OF CORRECTION

PATENT NO. : 5,652,197            Page 1 of 2

DATED : July 29, 1997

INVENTOR(S) : Jean-Pierre Claude, Shuaib A. Khan, and Robert W. Mitchell

It is certified that error appears in the above-identified patent and that said Letters Patent is hereby corrected as shown below:

On the title page, under the heading labeled "References Cited", under the subheading labeled "U.S. PATENT DOCUMENTS", please insert -- 
| | | | |
|---|---|---|---|
| 4,066,786 | 1/1978 | Bent et al. | 424/313 |
| 4,075,002 | 2/1978 | Drewe et al. | 71/DIG.1 |
| 4,612,034 | 9/1986 | Kruger et al. | 71/86 |
| 4,931,080 | 6/1990 | Chan et al. | 71/86 |

--.

On the title page, under the heading labeled "References Cited", before the subheading labeled "OTHER PUBLICATIONS", please insert

--          FOREIGN PATENT DOCUMENTS

| | | |
|---|---|---|
| A-2 059 773 | 1/1983 | United Kingdom ... A01N 47/38 |
| A-2 047 098 | 2/1983 | United Kingdom ... A01N 59/02 |
| A-2 115 420 | 12/1985 | United Kingdom . |
| WO 87/04595 | 8/1987 | WIPO ............ A01N 57/20 |
| 0 274 369A1 | 7/1988 | European Pat. Off. . A01N 57/20 |
| 0 357 553A2 | 7/1990 | European Pat. Off. . A01N 57/20 |

--.

UNITED STATES PATENT AND TRADEMARK OFFICE
CERTIFICATE OF CORRECTION

PATENT NO. : 5,652,197

DATED : July 29, 1997

INVENTOR(S) : Jean-Pierre Claude, Shuaib A. Khan, and Robert W. Mitchell

It is certified that error appears in the above-indentified patent and that said Letters Patent is hereby corrected as shown below:

On the title page, under the heading labeled "References Cited", under the subheading labeled "OTHER PUBLICATIONS", please insert -- Fiedler, H. P., "Lexikon der Hilfstoffe fur Pharmazie, Kosmetik und angrenzende Gebiete," 2nd Ed., Vol. 1, pp. 331-334, Aulendorf, Germany, 1981. --.

Signed and Sealed this

Twenty-first Day of October 1997

Attest:

BRUCE LEHMAN

Attesting Officer

Commissioner of Patents and Trademarks